United States Patent
Mastaloudis et al.

(10) Patent No.: US 9,072,780 B2
(45) Date of Patent: Jul. 7, 2015

(54) ORAL FORMULATIONS FOR COUNTERACTING EFFECTS OF AGING

(75) Inventors: Angela Mastaloudis, Holladay, UT (US); Steve Wood, Santaquin, UT (US); Richard Weindruch, Madison, WI (US); Tomas Alberto Prolla, Madison, WI (US); Jamie Louis Barger, Verona, WI (US); Mark Bartlett, Orem, UT (US); Scott B. Ferguson, Highland, UT (US); Joseph Chang, Sandy, UT (US)

(73) Assignee: NSE Products, Inc., Provo, UT (US)

( * ) Notice: Subject to any disclaimer, the term of this patent is extended or adjusted under 35 U.S.C. 154(b) by 525 days.

(21) Appl. No.: 13/115,027

(22) Filed: May 24, 2011

(65) Prior Publication Data
US 2012/0134976 A1 May 31, 2012

Related U.S. Application Data

(60) Provisional application No. 61/347,789, filed on May 24, 2010.

(51) Int. Cl.
| | |
|---|---|
| A61K 45/06 | (2006.01) |
| A23L 1/30 | (2006.01) |
| A61K 31/221 | (2006.01) |
| A61K 36/185 | (2006.01) |
| A61K 36/258 | (2006.01) |
| A61K 36/41 | (2006.01) |
| A61K 36/79 | (2006.01) |

(Continued)

(52) U.S. Cl.
CPC .............. *A61K 45/06* (2013.01); *A23L 1/3002* (2013.01); *A23V 2002/00* (2013.01); *A61K 31/221* (2013.01); *A61K 36/185* (2013.01); *A61K 36/258* (2013.01); *A61K 36/41* (2013.01); *A61K 36/79* (2013.01); *A61K 36/82* (2013.01); *A61K 36/87* (2013.01); *A61Q 19/08* (2013.01); *A61K 8/97* (2013.01); *A61K 2800/5922* (2013.01); *A61K 2800/92* (2013.01)

(58) Field of Classification Search
IPC .............................. A61K 36/61,36/258, 36/068
See application file for complete search history.

(56) References Cited

U.S. PATENT DOCUMENTS

| 6,569,624 B1 | 5/2003 | Weindruch et al. |
| 2003/0032030 A1 | 2/2003 | Prolla et al. |

(Continued)

FOREIGN PATENT DOCUMENTS

| CN | 1185908 A | 1/1998 |
| CN | 1355048 A | 6/2002 |

(Continued)

OTHER PUBLICATIONS

Tan et al., "ageLOC Recharge improves memory and learning ability in memory impairment models," FASEB J, vol. 24, Apr. 2010, meeting abstract.*

(Continued)

*Primary Examiner* — Rosanne Kosson
(74) *Attorney, Agent, or Firm* — Thorpe North & Western, LLP

(57) ABSTRACT

An oral formulation as described herein can comprise pomegranate extract, panax ginseng extract, and *c. sinensis*, where each is present in an amount effective to counteract and/or prevent effects of aging in a subject when administered to the subject. The effects of aging can include age-related changes in gene expression.

55 Claims, 5 Drawing Sheets

(51) Int. Cl.
*A61K 36/82* (2006.01)
*A61K 36/87* (2006.01)
*A61Q 19/08* (2006.01)
*A61K 8/97* (2006.01)

(56) References Cited

U.S. PATENT DOCUMENTS

| | | |
|---|---|---|
| 2006/0068438 A1 | 3/2006 | Prolla et al. |
| 2009/0252796 A1 | 10/2009 | Mazed et al. |
| 2009/0291156 A1 | 11/2009 | Liu |
| 2010/0015109 A1 | 1/2010 | Bias |
| 2010/0119463 A1 | 5/2010 | Jacobs |

FOREIGN PATENT DOCUMENTS

| | | |
|---|---|---|
| CN | 101361896 A | 11/2009 |
| JP | 2003/274888 | 9/2003 |
| JP | 2003/292429 | 10/2003 |
| JP | 2006/312594 | 11/2006 |
| JP | 2009/143886 | 7/2009 |
| KR | 2003/0055950 | 7/2003 |
| KR | 2004/0097589 | 11/2004 |
| KR | 2004/0101694 | 12/2004 |
| WO | WO 2008/147111 A2 | 12/2008 |

OTHER PUBLICATIONS

Meyers et al.; Perspectives on Translation Biology; Methods for Transcriptional Profiling in Plants. Be Fruitful and Replicate; Plant Physiology; Jun. 2004; pp. 637-652; vol. 135.

Masternak et al.; PPARs in Calorie Restricted and Genetically Long-Lived Mice; Hindawi Publishing Corporation, PPAR Research, vol. 2007, Article ID 28436, 7 pages.

PCT Application PCT/US2011/037797; filing date May 24, 2011; Angela Mastaloudis; International Search Report mailed Feb. 10, 2012.

Wu, Zimei et al., "ageLOC Recharge improves memory and learning ability in memory impairment models" FASEB journal, 2012; vol. 26:1095.1 (Correct Abstract).

Wu, Zimei et al., "ageLOC Recharge improves memory and learning ability in memory impairment models" FASEB journal, Apr. 2010; vol. 24 (Conference on Experimental Biology, Anaheim, CA, USA, Apr. 24-28, 2010; Amer Assoc Anatomists (AAA)); Amer Physiol Society (APS); Amer Soc Biochem (Incorrect Abstract).

\* cited by examiner

ORAL FORMULATIONS FOR COUNTERACTING EFFECTS OF AGING

RELATED APPLICATIONS

This application claims the benefit of U.S. Provisional Patent Application No. 61/347,789, which was filed on May 24, 2010 and which is incorporated in its entirety herein by reference.

BACKGROUND

One way in which the aging process can manifest itself at the organismal level is declining function in a number of areas, including sexual performance, metabolic efficiency and capacity, cognitive ability, and sensory dynamic range. While the bases underlying such decline is not fully understood, it is recognized that these often are due in part to age-related changes in organs and tissues. For example, age-related changes in human and rodent hearts include a reduction in the number of myocytes, myocyte hypertrophy, cardiac fibrosis, lipofuscin pigment accumulation, a reduction in calcium transport across sarcoplasmic reticulum membrane, and alterations in the response to adrenergic stimulation. Collectively, these alterations can contribute to age-related heart disease.

Such changes can in turn be a function of changes in the various cell types that make up tissues and contribute to their function in organ systems. The activity, structure, and identity of a cell arises from its specific protein complement, as regulated by gene expression. As such, age-related changes in cellular structure and function likely find a basis in changes in genetic expression. Therefore, aging can be reflected in genetic function.

Through increasingly more sophisticated methods of measuring gene expression, it has become possible to identify genetic correlates of aging. For example, the use of whole genome transcriptional profiling, DNA microarrays, and quantitative PCR (qPCR), it is possible to identify transcriptional biomarkers of aging and to quantify the effects of aging on their expression. Interventions that retard or counteract these effects can therefore be beneficial in counteracting organismal aging.

SUMMARY OF THE INVENTION

According to an embodiment, an oral formulation can include pomegranate extract, *panax ginseng* extract, and *c. sinensis*, where each is present in an amount effective to counteract effects of aging in a subject when administered to the subject. In an aspect of the embodiment, the formulation is more effective to counteract the effects in the subject to a greater degree than any one of pomegranate extract, *panax ginseng* extract, and *c. sinensis*. In another embodiment, an oral formulation can include pomegranate extract at about 0.09 wt % to about 80.32 wt %; *c. sinensis* at about 13.46 wt % to about 99.67 wt %; and *panax ginseng* extract at about 0.19 wt % to about 67.72 wt %.

According to an embodiment, a method of counteracting an effect of aging in a subject, comprises administering to the subject an effective amount of an oral formulation comprising pomegranate extract, *panax ginseng* extract, and/or *c. sinensis*. In an aspect of the method, administration of an effective amount of formulation is more effective to counteract the effects in the subject than administering the same amount of any one of pomegranate extract, *panax ginseng* extract, and *c. sinensis*.

In another embodiment, a method of counteracting age-related changes in gene expression in muscle tissue of a subject comprises administering to the subject an effective amount of an oral formulation comprising *c. sinensis*.

In still another embodiment, a method of counteracting age-related changes in gene expression in brain tissue of a subject, comprises administering to the subject an effective amount of an oral formulation comprising a pomegranate extract.

DETAILED DESCRIPTION OF EXAMPLE EMBODIMENTS

Figure 1:
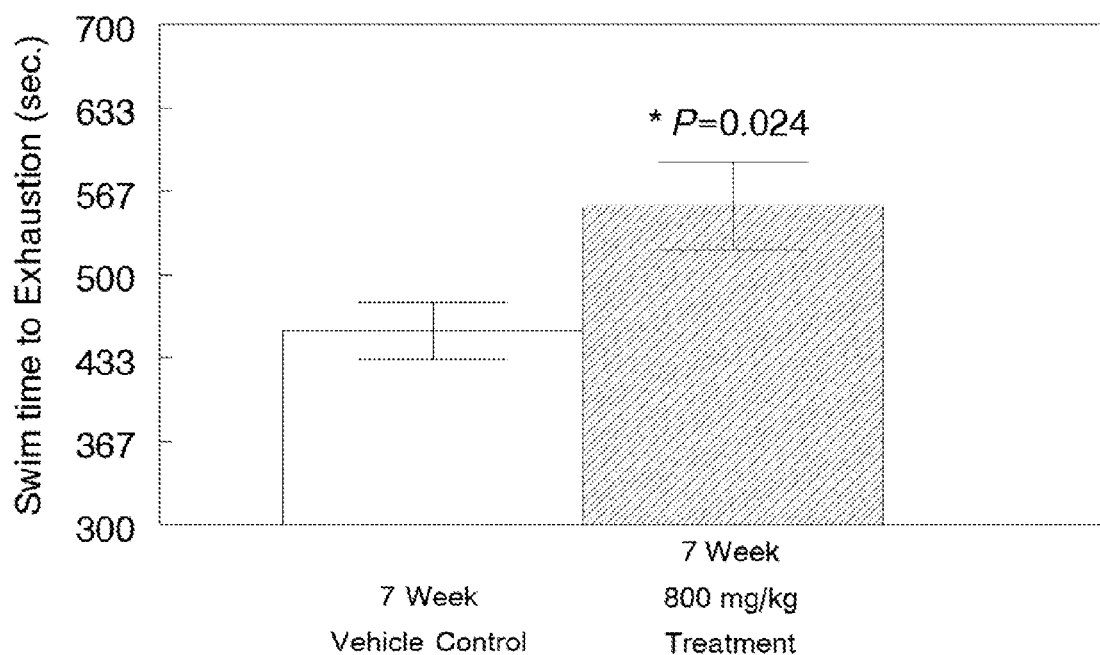
FIG. 1 is a bar graph comparing endurance in mice receiving a formulation in accordance with an embodiment to mice receiving vehicle only.

In describing and claiming the present invention, the following terminology will be used.

The singular forms "a," "an," and "the" include plural referents unless the context clearly dictates otherwise. Thus, for example, reference to "a carrier" includes reference to one or more of such carriers, and reference to "an excipient" includes reference to one or more of such excipients.

As used herein, "aging" and "senescence" may be used interchangeably to the accumulation of changes that occur in a living organism over time. Such changes can range from those affecting genetic and cellular function to those affecting the function of organs, organ systems, or the whole organism. Senescence in particular refers to such changes occurring after an organism has attained biological maturity and which may progress until the eventual death of the organism. The term "effects of aging" herein particularly to refers to age-related changes in genetic function, such as changes in transcription of individual genes as well as transcriptional profiles of groups of genes.

As used herein, the term "biomarkers of aging" refers generally to genes or gene groups the expression of which is consistently found to change with age, and their transcriptional products. Such genes and gene groups may be referred to as "genetic biomarkers" while the transcriptional products may be referred to as "transcriptional biomarkers."

As used herein, "up-regulation" and "down-regulation" refer respectively to increased or decreased expression of one or more genes and as a result the protein(s) encoded by those genes, usually in response to some signal or condition. In particular reference to biomarkers of aging, up-regulation and down-regulation respectively refer to such increases or decreases in response to age.

As used herein, "formulation" and "composition" may be used interchangeably, and refer to a combination of two or more elements, or substances. In some embodiments a composition may include an active agent in combination with a carrier or other excipients, adjuvants, etc.

As used herein, "effective amount" refers to an amount of an ingredient which, when included in a composition, is sufficient to achieve an intended compositional or physiological effect. Thus, a "therapeutically effective amount" refers to a non-toxic, but sufficient amount of an active agent, to achieve therapeutic results in treating or preventing a condition for which the active agent is known to be effective. It is understood that various biological factors may affect the ability of a substance to perform its intended task. Therefore, an "effective amount" or a "therapeutically effective amount" may be dependent in some instances on such biological factors. Further, while the achievement of therapeutic effects may be measured by a physician or other qualified medical personnel using evaluations known in the art, it is recognized that individual variation and response to treatments may make the achievement of therapeutic effects a subjective decision. The determination of an effective amount is well within the ordinary skill in the art of pharmaceutical sciences and medicine.

As used herein, "pharmaceutically acceptable carrier," and "carrier" may be used interchangeably, and refers to any inert and pharmaceutically acceptable material with which a bioactive agent or a nutritional agent may be combined to achieve a specific dosage formulation for delivery to a subject. As a general principle, carriers must not react with the bioactive agent in a manner which substantially degrades or otherwise adversely affects the bioactive agent.

As used herein, "Cordyceps fungus" or "*c. sinensis*" refers to the fungus species *Cordyceps sinensis* including all anamorphs, strains, and hybrids thereof.

As used herein, "*p. hepiali*" or "*hepiali*" refers to the fungus *Paecilomyces hepiali* including all strains and hybrids thereof.

As used herein, "*h. sinensis*" or "*hirsutella*" refers to the fungus *Hirsutella sinensis* including all strains and hybrids thereof.

As used herein, "excipient" refers to substantially inert substance, which may be combined with an active agent and a carrier to achieve a specific dosage formulation for delivery to a subject, or to provide a dosage form with specific performance properties. For example, excipients may include binders, lubricants, etc., but specifically exclude active agents and carriers.

As used herein, "subject" refers to a mammal that may benefit from the administration of a composition or method as recited herein. Most often, the subject will be a human.

As used herein, "administration," and "administering" refer to the manner in which an active agent, or composition containing such, is presented to a subject. Administration can be accomplished by various routes well-known in the art such as oral and non-oral methods.

As used herein, "oral administration" refers to a route of administration that can be achieved by swallowing, chewing, or sucking of an oral dosage form comprising the drug. Examples of well-known oral dosage forms include tablets, capsules, caplets, powders, granulates, beverages, syrups, elixirs, confections, or other food items, etc.

Concentrations, amounts, solubilities, and other numerical data may be presented herein in a range format. It is to be understood that such range format is used merely for convenience and brevity and should be interpreted flexibly to include not only the numerical values explicitly recited as the limits of the range, but also to include all the individual numerical values or sub-ranges encompassed within that range as if each numerical value and sub-range is explicitly recited.

For example, a concentration range of 0.5 to 400 should be interpreted to include not only the explicitly recited concentration limits of 0.5 and 400, but also to include individual concentrations within that range, such as 0.5, 0.7, 1.0, 5.2, 8.4, 11.6, 14.2, 100, 200, 300, and sub-ranges such as 0.5-2.5, 4.8-7.2, 6-14.9, 55, 85, 100-200, 117, 175, 200-300, 225, 250, and 300-400, etc. This interpretation should apply regardless of the breadth of the range or the characteristic being described.

As used herein, the term "about" means that dimensions, formulations, parameters, and other quantities and characteristics are not and need not be exact, but may be approximated and/or larger or smaller, as desired, reflecting tolerances, conversion factors, rounding off, measurement error and the like and other factors known to those of skill. Further, unless otherwise stated, the term "about" shall expressly include "exactly," consistent with the discussion above regarding ranges and numerical data.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

A method of counteracting effects of aging in a subject can comprise administering to the subject an effective amount of an oral formulation comprising active agents that are effective to provide such a result. In particular, oral formulations for counteracting or retarding effects of aging in a subject can comprise one or more active agents that are effective in retarding or counteracting age-related changes in gene expression. According to an embodiment, such an oral formulation can comprise pomegranate extract, and optionally, a *panax ginseng* extract, and/or a *c. sinensis*, each present in an amount effective to counteract effects of aging in a subject when administered to the subject.

In a given organism one can identify genes and gene products that act as biomarkers of aging. Expression of particular genes and groups of genes are found to change, sometimes dramatically, as the organism ages. These genes can be identified by assaying their transcriptional products by available methods. The particular biomarkers of aging can depend on the organism. That is, the identity of genes that show age-related effects can differ from species to species. In addition the identity of biomarkers and the degree of age-related effects on the expression of each biomarker can differ among tissue types in an organism. For example, a gene or gene group may be a consistent biomarker of aging in muscle tissue while showing lesser age-related effects in brain tissue, and no age-related effects at all in other tissues.

The effect of aging on gene expression depends in part on the gene itself, particularly on the function associated with the gene. Therefore, in some genes expression is found to up-regulate with age, while in others expression down-regulates with age. In addition, the degree of up-regulation or down-regulation observed can differ from gene to gene, with some exhibiting dramatic changes while others exhibit changes that are more subtle but still significant. Gene expression may vary from tissue to tissue. For example, a gene such as PPA-Ralpha may be up-regulated with age in the liver, but may be down-regulated with age in the skeletal muscle.

The inventors have found that formulations according to embodiments herein are effective in counteracting age-related changes among the genetic biomarkers of aging. In a specific aspect, in genes exhibiting age-related up-regulation, a formulation can decrease or reverse said up-regulation. In another aspect, the formulation can decrease or reverse age-related down-regulation in genes exhibiting such a down-regulation. In a particular embodiment, an oral formulation can comprise a plurality of different active agents selected to counteract age-related effects in a number of different tissues. In another embodiment, a method for counteracting changes in gene expression that are associated with aging of a subject can comprise administering to the subject an effective amount of a formulation that includes pomegranate extract, *panax ginseng* extract, and *c. sinensis*. In a particular embodiment, such changes can occur in vitro. In some aspects the ginseng extract and *c. sinensis* ingredients are optional and either one or the other or both may be added in order to achieve a desired result.

The ingredients described herein can exhibit an enhanced effectiveness when provided in combination. In a particular aspect, a formulation containing a combination of pomegranate extract, *panax ginseng* extract, and *c. sinensis* is more effective in counteracting aging-related changes in gene expression than expected based on the individual efficacies of the ingredients. For example, an amount of the formulation can be more effective to counteract aging-related changes in gene expression than the same amount of any one of pomegranate extract, *panax ginseng* extract, or *c. sinensis*. In another example, an amount of the formulation can be more effective than the same amount of any two of these ingredients.

To determine biomarkers of aging in an organism one can obtain global gene expression profiles by monitoring mRNA levels for multiple genes, using high-density oligonucleotide arrays. More specifically, oligonucleotide arrays can be used to assay samples from subjects of increasing age, and the resulting signals compared to ascertain which of the detected genes show changed expression with age. Using this approach one can identify genetic biomarkers and also quantify age-related effects. One can further ascertain how various treatments may modify these age-related effects. For example, one treatment that has been found to increase maximum lifespan and slow multiple aspects of the aging process in diverse species is dietary caloric restriction. However, adhering to a low-calorie diet is often difficult and presents a danger of vitamin deficiency and malnutrition, making this not a widely accessible approach to counteract aging. The agents described herein have been found to be as effective as or even to surpass caloric restriction in reducing age-related effects on gene expression. An oral formulation comprising these agents can provide an anti-aging measure that is available to a wide array of subjects.

The oral formulation can include an effective amount of pomegranate extract. In a particular embodiment, pomegranate extract can be present at from about 0.09 wt % to about 80.32 wt % of the total formula. In a more particular embodiment, pomegranate extract can be present at from about 3.0 wt % to about 20.0 wt %. In a still more particular embodiment, pomegranate extract is present at from about 6.5 wt % to about 8.0 wt %. The pomegranate extract used in the formulation can be obtained from pomegranate fruit by known extraction methods. In a particular example, pomegranate extract is extracted from fresh pressed whole pomegranate fruit solids (*Punica granatum*, Wonderful cultivar) with hot water. The inventors have found that polyphenols present in pomegranate can provide a number of health benefits, including effectively counteracting age-related effects on gene expression. In a particular embodiment, the oral formulation contains at least 85% pomegranate polyphenols.

The oral formulation can also include an effective amount of the fungus *Cordyceps sinensis*. In a particular embodiment, *c. sinensis* is present in the formulation at about 13.46 wt % to about 99.67 wt % of the total formulation. In a more particular embodiment, *c. sinensis* is present at from about 50.0 wt % to about 95.0 wt %. In a still more particular embodiment, *c. sinensis* is present at from about 83.0 wt % to about 89.0 wt %. The inventors have found that *Cordyceps sinensis* also can counteract age-related effects on gene expression. Two anamorph strains found in the mycelium of Cordyceps fungus, *h. sinensis* and *p. hepialis*, are effective in providing the beneficial outcomes associated with Cordyceps fungus, and can be obtained from artificially cultivated mycelium. In a particular embodiment, the oral formulation can include at least one of *p. hepialis* and/or *h. sinensis*, or alternatively extracts thereof.

The oral formulation can further include an extract of *panax ginseng*. In a particular embodiment, *panax ginseng* extract is present in the formulation at about 0.19 wt % to about 67.72 wt % of the total formulation. In a more particular embodiment, *panax ginseng* extract is present at from about 1.0 wt % to about 20.0 wt %. In a still more particular embodiment, *panax ginseng* extract is present at from about 3.5 wt % to about 5.0 wt %. *Panax ginseng* includes levels of active ginsenosides which mediate its effects in a subject to which it is administered. In an aspect, the extract can come from one or more parts of the ginseng root. Naturally, the ginseng main root contains a ginsenoside ratio of Rg1 saponin (protopanaxatriol) to the saponin Rb1 (protopanaxadiol) of 1.0. In contrast, the less abundant ginseng root hair has a higher concentration of the Rb1, resulting in a Rb1/Rg1 of ~4.6. The ginsenoside Rb1 can provide benefits such as calming, decreased anxiety, physical performance, and mental focus, while excessive levels of Rg1 is thought to contribute to less positive side effects. In a particular embodiment, main root extract and root hair extract can be mixed to control the level of Rg1 while increasing the level of the Rb1, and so maintain a desired Rb1/Rg1 ratio. The result is a ginseng extract with a ratio of the biologically active ginsenosides Rb1 and Rg1 that supports mental and physical performance and provides anti-stress benefits without side effects. In a particular embodiment, the *panax ginseng* extract present in the oral formulation includes ginsenoside Rb1 and ginsenoside Rg1 at a ratio of about 3:1 to about 5:1. In a more particular embodiment, the Rb1 to Rg1 ratio is about 4.5:1 to about 4.7:1.

The oral formulation can be formulated to provide an effective amount of the active agents in accordance with a particular dosage regimen. The oral formulations herein can provide each of the active agents according to a desired daily dose. In a specific embodiment, the oral formulation is provided in a dosage form containing from about 140 mg to about 200 mg pomegranate extract, from about 70 mg to about 130 mg *panax ginseng* extract, and from about 1800 mg to about 2200 mg *c. sinensis*. In another aspect, the oral formulation can be administered to a subject so as to deliver a desired amount of active agent on a per body weight basis. Administration can be configured based on the species of subject (e.g. a mammalian subject, or more specifically a human subject), as well as other factors such as sex, age, medical condition, and the like. In a particular embodiment, an effective amount of the oral formulation delivers to the subject a daily dose comprising about 0.15 mg/kg to about 30.0 mg/kg of pomegranate extract, about 0.35 mg/kg to about 15 mg/kg of *panax ginseng* extract, and about 15.0 mg/kg to about 150.0 mg/kg of *c. sinensis*.

In addition to the principal agents such as pomegranate extract, ginseng, and *c. sinensis*, further active agents can be included in the formulation. These can include agents that are also effective against aging in particular, as well as agents that provide other health benefits when administered to a subject. In a particular embodiment, the oral formulation can comprise at least one of Schizandra berry extract, whole grape extract, CoenzymeQ$_{10}$, Rhodiola rosacea extract, Tart cherry extract, and L-carnitine tartrate. These agents each have beneficial properties that make them suitable for inclusion in health supplements in general and anti-aging formulation as a particular example. However, the list is not meant to be exhaustive, and other pharmaceutically acceptable additives as known in the art are contemplated for inclusion in the formulation. In a particular example, additional active agents are selected to provide effects that contribute to counteracting effects of aging.

The oral formulation can be prepared in any delivery or dosage form suited for oral administration. For example the active agents in the formulation can be combined with a liquid carrier and then concentrated or diluted to prepare a liquid form. Alternatively, the active agents can be dried, processed, and combined with appropriate materials such as fillers, tabletting agents, plasticizers, and the like for preparation of a solid dosage form. Solid and liquid dosage forms known in the food and pharmaceutical arts are contemplated to be used, such as capsules, tablets, powders, beverages, wafers, confectionaries, chewables, gels, pastes, elixirs, syrups, drops, lozenges, and the like. In a particular embodiment, the oral formulation is processed into a powder that may optionally include sweeteners and flavors and is dissolvable in water or other liquid to create a beverage. In another particular embodiment, the oral formulation is processed and placed in a capsule, such as a gelatin capsule.

The oral formulation can further include one or more excipients as called for to prepare a delivery form. A variety of excipients commonly known in the pharmaceutical and food industry for making various dosage forms may be used. These include, for example, liquid carriers, solvents, fillers, binders, lubricants, glidants, flavorings, and colorings. In a particular embodiment, the oral formulation includes one or more of food grade gum, anti-caking agents, lecithin, microcrystalline cellulose, silica gel, flavoring, and sweetener. Food grade gums include xanthar gum and guar gum. Anti-caking agents include, without limitation, silicon dioxide, stearic acid, tricalcium phosphate, calcium silicate, sodium aluminosilicate, magnesium carbonate, talc, bentonite, sodium ferrocyanide, potassium ferrocyanide, and bone phosphate.

While not wishing to be bound to a particular theory, it is expected that the effects of aging on the expression of certain genes is connected to manifestations of senescence at the organismal level. Stated another way, the transcriptional products of genetic biomarkers of aging are believed to be involved in physiological functions that deteriorate with age. Therefore, the retardation of aging effects on gene expression obtained by administering the formulation to a subject can also be realized in physiological outcomes in the subject. In a particular embodiment, the oral formulation counteracts effects of aging, such as age-related decline in physical vigor and endurance, sexual performance, sexual capacity, energy metabolism, cognitive function, sleep duration and quality, memory formation and retention, and the like.

In an embodiment, an oral formulation as described herein can counteract effects of aging in particular tissues in a subject or in a plurality of tissues. In one aspect, said formulation can lessen or reverse effects of age in gene expression in biomarkers of aging found in particular tissues. This effect can be produced by administration of the formulation to the subject, or alternatively, by directly treating the tissue with the formulation. In another aspect, the formulation can counteract age-related effects on physiological function that manifest in particular tissues. In still another aspect, the formulation can counteract effects of age on function at the organismal level by acting on one or more tissues that contribute to said function. Declining function of different types can be related to deterioration in particular tissues or systems. For example, decreased physical strength and endurance can arise in part from age-related effects in muscle tissue and overall metabolic capacity, while decreased cognitive function can be related to changes in related areas of the brain. The oral formulations described herein can comprise agents that provide particular anti-aging effects in particular tissues, including but not limited to the brain, skeletal muscle, cardiac muscle, gonadal tissue, connective tissue, skin, digestive system, and endocrine glands.

The aspects of the present invention are illustrated further by the following exemplary embodiments. These examples should not be considered as limitations of the disclosure, but are merely in place to instruct those skilled in the art in practicing the invention. It will be apparent to those of ordinary skill in the art that numerous modifications in form, usage and details of implementation can be made without the exercise of inventive faculty, and without departing from the principles and concepts of the invention. Accordingly, it is not intended that the invention be limited, except as by the claims set forth below.

EXAMPLES

Example 1

Testing Effects of Cordyceps Administration on Gene Expression in Skeletal Muscle (Gastrocnemius), General Protocol C57BL/6J mice were obtained at 18 months of age, individually housed in shoebox cages, and provided with 24 grams (~84 kcal) of AIN-93M diet per week (7 grams on Monday and Wednesday and 10 grams on Friday). Starting at 21 months of age and continuing until 25 months of age, mice were either maintained on the AIN93M diet (Old Controls, OC) or were assigned to an AIN93M diet supplemented with *Cordyceps sinensis* (3.063 grams per kilogram diet). Young Control C57BL/6J mice (YC) were obtained at six weeks of age and maintained on the AIN93M diet until five months of age. At the specified ages, tissues were collected from the gastrocnemius skeletal muscle of the mice, flash-frozen in liquid nitrogen and stored at −80° C. for later analysis.

Gene expression profiling was used to identify individual genes and functional classes of genes that were changed with age and/or Cordyceps treatment.

Total RNA was extracted from frozen tissue by using TRIZOL™ reagent (Life Technologies, Grand Island, N.Y.). Polyadenylate [poly(A)+] RNA was purified from the total RNA with oligo(dT)-linked oligotex resin (Qiagen, Valencia, Calif.). One microgram of poly(A)+ RNA was converted into double-stranded cDNA (dscDNA) by using the SuperScript Choice System™ (Life Technologies) with an oligo(dT) primer containing a T7 RNA polymerase promoter (Genset, La Jolla, Calif.). dscDNA was extracted with phenolchloroform-isoamyl alcohol and precipitated with pellet paint coprecipitant (Novagen). Biotin-labeled RNA was synthesized in vitro by using the BioArray™ High Yield RNA Transcript Labeling Kit (Enzo, Farmingdale, N.Y.). The biotin-labeled antisense cRNA was purified using the RNeasy affinity column (Qiagen), and fragmented randomly. The hybridization cocktail (200 µl) containing 10 µg of fragmented cRNA was injected into a Mouse 1.0 Gene ST™ array (Affymetrix, Santa Clara, Calif.). The gene chip was placed in a 45° C. oven at 60 rpm for 16 h. After hybridization, the gene chips were washed and stained in a fluidic station (Model 800101, Affymetrix) with signal amplification protocol using antibody. DNA chips were scanned at a resolution of 3 μm twice by using a Hewlett-Packard GeneArray™ Scanner (Model 900154, Affymetrix), and the averaged images were used for further analysis.

Affymetrix Algorithm™ software was used to determine the presence of mRNA in samples and compute the signals of probe sets. To identify changes in expression that occurred with age, the average value of the OC samples was compared with the average value of the YC; to determine changes in expression with Cordyceps treatment, the average value of the Cordyceps-treated samples was compared to the age-matched OC samples. Two-tailed t-tests (assuming equal variance) were used to determine if the change in expression for individual genes was statistically significant. The magnitude of the change in expression is reported as "fold change" (FC) values which were $\log_2$-adjusted to fit normality assumptions for statistical analyses.

To identify functional classes of genes changed with age and/or Cordyceps, Parametric Analysis of Gene set Enrichment (PAGE) was used as described in Kim and Volsky (2005), PAGE: Parametric Analysis of Gene Set Enrichment, BMC Bioinformatics, 6:144. This approach can be useful to identify pathways modulated by treatment when changes in gene expression are modest but consistent. Annotations from the Gene Ontology (GO) consortium (http://www.geneontology.org) were used to link individual genes with their function, though limited to only those annotations from "Level 3" or greater, and that were represented by more than 10 but less than 1000 genes. At the time of the analysis, there were 2,884 GO terms fitting these criteria. The PAGE technique also calculates a z-score for each GO term, with positive values indicating that a GO term was up-regulated with treatment and negative values indicating down-regulation of a GO term by treatment.

Example 2

Effects of Cordyceps Administration to Oppose Age-Related Changes in Skeletal Muscle Gene Groups Related to Behavior and Sexual Vitality The effect of Cordyceps administration on expression in functional gene groups in skeletal muscle associated with sexual vitality was tested using the protocol in Example 1. The results (z-scores for age and treatment, statistical significance, and change in age-related effects due to treatment) are shown in Table 1:

TABLE 1

| GO Term & ID | # genes | z-score, Age | z-score, Cordyceps | P-value, Age | P-value, Cordyceps | Difference, Old vs Cordyceps |
|---|---|---|---|---|---|---|
| endocrine system development GO: 0035270 | 67 | −3.135 | 2.795 | 0.002 | 0.005 | −5.93 |
| hormone activity GO: 0005179 | 103 | −3.937 | 1.370 | 0.000 | 0.171 | −5.31 |
| neuropeptide hormone activity GO: 0005184 | 15 | −3.176 | 2.067 | 0.001 | 0.039 | −5.24 |
| regulation of behavior GO: 0050795 | 13 | −1.863 | 3.284 | 0.062 | 0.001 | −5.15 |
| behavior GO: 0007610 | 339 | −0.942 | 3.962 | 0.346 | 0.000 | −4.90 |
| regulation of hormone levels GO: 0010817 | 113 | −1.676 | 2.818 | 0.094 | 0.005 | −4.49 |
| regulation of steroid hormone receptor signaling pathway GO: 0033143 | 11 | −1.274 | 3.114 | 0.203 | 0.002 | −4.39 |
| reproductive behavior GO: 0019098 | 15 | −1.621 | 2.658 | 0.105 | 0.008 | −4.28 |
| pheromone receptor activity GO: 0016503 | 94 | 0.501 | −5.301 | 0.616 | 0.000 | 5.80 |
| response to pheromone GO: 0019236 | 97 | 0.511 | −5.510 | 0.609 | 0.000 | 6.02 |

Example 3

Effects of Cordyceps Administration to Oppose Age-Related Changes in Skeletal Muscle Gene Groups Related to Energy Metabolism and Physical Energy The effect of Cordyceps administration on expression in functional skeletal muscle gene groups associated with physical energy and mitochondrial function was tested using the protocol in Example 1. The results are shown in Table 2:

TABLE 2

| GO Term & ID | # genes | z-score, Age | z-score, Cordyceps | P-value, Age | P-value, Cordyceps | Difference, Old vs Cordyceps |
|---|---|---|---|---|---|---|
| regulation of cAMP biosynthetic process GO: 0030817 | 52 | −3.173 | 2.486 | 0.002 | 0.013 | −5.659 |
| skeletal system morphogenesis GO: 0048705 | 117 | −2.832 | 2.690 | 0.005 | 0.007 | −5.523 |
| skeletal system development GO: 0001501 | 252 | −2.603 | 2.707 | 0.009 | 0.007 | −5.310 |
| muscle cell differentiation GO: 0042692 | 67 | −1.669 | 3.636 | 0.095 | 0.000 | −5.305 |
| activation of adenylate cyclase activity GO: 0007190 | 35 | −3.054 | 2.022 | 0.002 | 0.043 | −5.076 |
| carbohydrate catabolic process GO: 0016052 | 70 | −2.475 | 2.599 | 0.013 | 0.009 | −5.074 |
| glucose metabolic process GO: 0006006 | 97 | −2.634 | 2.002 | 0.008 | 0.045 | −4.636 |
| locomotory behavior GO: 0007626 | 208 | 0.300 | 4.516 | 0.764 | 0.000 | −4.216 |
| gluconeogenesis GO: 0006094 | 16 | −2.287 | 1.721 | 0.022 | 0.085 | −4.008 |
| mitochondrial intermembrane space GO: 0005758 | 13 | 1.452 | −2.737 | 0.146 | 0.006 | 4.190 |
| mitochondrial large ribosomal subunit GO: 0005762 | 16 | 1.777 | −3.110 | 0.076 | 0.002 | 4.887 |
| mitochondrial part GO: 0044429 | 369 | 0.019 | −5.794 | 0.985 | 0.000 | 5.813 |
| mitochondrial matrix GO: 0005759 | 42 | 1.413 | −4.588 | 0.158 | 0.000 | 6.001 |
| ATPase activity, coupled GO: 0042623 | 173 | 4.219 | −2.050 | 0.000 | 0.040 | 6.269 |
| mitochondrial ribosome GO: 0005761 | 31 | 1.739 | −4.566 | 0.082 | 0.000 | 6.305 |
| ATPase activity GO: 0016887 | 215 | 4.839 | −2.122 | 0.000 | 0.034 | 6.961 |

Example 4

Effects of Cordyceps Administration to Oppose Age-Related Changes in Skeletal Muscle Gene Groups Related to Mental Vitality The effect of Cordyceps administration on expression in functional skeletal muscle gene groups associated with mental vitality was tested using the protocol in Example 1. The results are shown in Table 3:

TABLE 3

| GO Term & ID | # genes | z-score, Age | z-score, Cordyceps | P-value, Age | P-value, Cordyceps | Difference, Old vs Cordyceps |
|---|---|---|---|---|---|---|
| neurogenesis GO: 0022008 | 465 | −5.670 | 5.832 | 0.000 | 0.000 | −11.502 |
| neuropeptide signaling pathway GO: 0007218 | 70 | −3.563 | 2.965 | 0.000 | 0.003 | −6.528 |

TABLE 3-continued

| GO Term & ID | # genes | z-score, Age | z-score, Cordyceps | P-value, Age | P-value, Cordyceps | Difference, Old vs Cordyceps |
|---|---|---|---|---|---|---|
| neuropeptide hormone activity GO: 0005184 | 15 | −3.176 | 2.067 | 0.001 | 0.039 | −5.243 |
| behavior GO: 0007610 | 339 | −0.942 | 3.962 | 0.346 | 0.000 | −4.905 |
| memory GO: 0007613 | 25 | −2.175 | 2.660 | 0.030 | 0.008 | −4.835 |
| learning or memory GO: 0007611 | 76 | −2.556 | 2.278 | 0.011 | 0.023 | −4.834 |
| associative learning GO: 0008306 | 15 | −2.650 | 2.068 | 0.008 | 0.039 | −4.718 |
| visual learning GO: 0008542 | 26 | −1.801 | 2.329 | 0.072 | 0.020 | −4.130 |

Example 5

Effects of Cordyceps Administration to Oppose Age-Related Changes in Skeletal Muscle Gene Groups Related to Cellular Aging The effect of Cordyceps administration on expression in functional skeletal muscle gene groups associated with cellular and genetic maintenance processes was tested using the protocol in Example 1. The results are shown in Table 4:

TABLE 4

| GO Term & ID | # genes | z-score, Age | z-score, Cordyceps | P-value, Age | P-value, Cordyceps | Difference, Old vs Cordyceps |
|---|---|---|---|---|---|---|
| growth factor activity GO: 0008083 | 130 | −2.838 | 3.703 | 0.005 | 0.000 | −6.542 |
| multicellular organismal response to stress GO: 0033555 | 34 | −2.319 | 3.140 | 0.020 | 0.002 | −5.459 |
| telomere maintenance GO: 0000723 | 17 | 2.238 | −1.963 | 0.025 | 0.050 | 4.201 |
| telomere organization GO: 0032200 | 17 | 2.238 | −1.963 | 0.025 | 0.050 | 4.201 |
| cell redox homeostasis GO: 0045454 | 53 | 2.673 | −1.680 | 0.008 | 0.093 | 4.352 |
| cellular response to stress GO: 0033554 | 322 | 3.818 | −1.849 | 0.000 | 0.065 | 5.666 |
| cellular response to DNA damage stimulus GO: 0034984 | 225 | 3.800 | −2.739 | 0.000 | 0.006 | 6.539 |
| DNA repair GO: 0006281 | 200 | 3.653 | −2.901 | 0.000 | 0.004 | 6.554 |
| response to DNA damage stimulus GO: 0006974 | 254 | 4.250 | −3.207 | 0.000 | 0.001 | 7.457 |

Example 6

Comparison of Effect of Caloric Restriction and Pomegranate Extract Administration on Gene Expression Biomarkers of Aging B6C3F1 hybrid mice were obtained and individually housed in shoebox cages and provided with 24 grams (~84 kcal) of AIN-93M diet per week (7 grams on Monday and Wednesday and 10 grams on Friday). At 14 months of age, mice assigned to one of three treatment groups until 30 months of age: Old Control (OC), maintained on the AIN93M diet; Calorie Restricted (CR), provided 63 kcal/week of a modified AIN93M formulation; Pomegranate (POM), the AIN93M formulation supplemented with 128 milligrams pomegranate extract per kilogram diet (POM Wonderful LLC, Los Angeles, Calif.). Young Control (YC) mice were also purchased at six weeks of age and maintained on the AIN93M diet until five months of age. At the specified ages, tissues were collected from mice, flash-frozen in liquid nitrogen and stored at −80° C. for later analysis.

Panels of tissue-specific gene expression biomarkers of age have been identified that can be used to quantify the extent to which an intervention slows aging at the transcriptional level. To determine if CR or POM opposed the aging process, we performed quantitative real-time PCR (RT-qPCR) analysis from RNA isolated from entire hearts, cerebral cortex and gastrocnemius skeletal muscle from all groups of mice. CR was used as a positive control in this experiment as caloric restriction is widely accepted as the only nutritional intervention to retard biological aging across a diverse range of species. Briefly, the magnitude of age-related change was determined for each gene (OC vs. YC) and the extent to which CR or POM opposed the aging change was calculated as the "percent prevention of aging" (i.e., 100% prevention of aging indicates that an intervention returned gene expression levels to that seen in the YC group). For each tissue, the "percent prevention of aging" values were averaged across all genes to calculate an "Aging Prevention Index" (API). Thus, the API gives an overall measure of the ability of a treatment to oppose aging.

TABLE 5

Cerebral cortex

| Gene | Prevention by CR | Prevention by POM |
| --- | --- | --- |
| Apod | −1% | 44% |
| B2m | 23% | 50% |
| C1qa | −17% | 46% |
| C1qb | 6% | 34% |
| Cd68 | 2% | 71% |
| Clec7a | 17% | 83% |
| Cst7 | 19% | 65% |
| Ctsd | −16% | 231% |
| Gfap | −9% | 33% |
| Il33 | −22% | 114% |
| Lgals3 | 16% | 61% |
| Lyzs | 19% | 8% |
| Spp | 7% | 10% |
| Aging Prevention Index (API) | 3% | 65% |

TABLE 6

Heart Muscle

| Gene | Prevention by CR | Prevention by POM |
| --- | --- | --- |
| Amy1 | 44% | 117% |
| Apod | −9% | −25% |
| Bdh1 | 6% | 274% |
| C3 | 31% | 1% |
| Ccl8 | 35% | 4% |
| Mt2 | 100% | 33% |
| Myot | −15% | 115% |
| Pah | 8% | 19% |
| Prkcq | −13% | −15% |
| Scap2 | 5% | −1% |
| Serpina3 | 73% | 39% |
| Vgll2 | 28% | −42% |
| Aging Prevention Index (API) | 24% | 43% |

TABLE 7

Gastrocnemius Skeletal Muscle

| Gene | Prevention by CR | Prevention by POM |
| --- | --- | --- |
| Amy1 | −15% | −89% |
| Apod | −41% | 153% |
| C4 | 51% | 124% |
| Cds1 | −3% | 199% |
| Col1a1 | 19% | 10% |
| Col1a2 | 22% | −14% |
| Col3a1 | 19% | −29% |
| Gadd45a | −27% | −16% |
| Igh6 | −17% | 3% |
| Lpar1 | 69% | 64% |
| Mt2 | 69% | 3% |

TABLE 7-continued

Gastrocnemius Skeletal Muscle

| Gene | Prevention by CR | Prevention by POM |
| --- | --- | --- |
| Prkcz | −22% | 30% |
| Rhpn2 | 28% | −2% |
| Syt9 | −12% | 14% |
| Aging Prevention Index (API) | 10% | 32% |

As shown in the data, administration of pomegranate extract produced at least a partial reversal in aging effects seen in biomarkers of age. Also, the overall effect of pomegranate extract was consistently greater than that produced by caloric restriction, an intervention widely accepted to retard biological aging.

Example 7

Effects of Pomegranate-Cordyceps-Ginseng Formulation on Endurance in Middle-Aged Female Mice Fifty-seven (57) female mice, 18 months old, were randomly assigned to one of two groups. Group 1 (n=29) was fed a regular chow diet ("vehicle"), while Group 2 (n=28) was fed a regular chow diet plus a blend of pomegranate extract, *panax ginseng* and *c. sinensis* (800 mg/kg diet, delivered by gavage). Feeding continued for seven weeks. Caloric intake was adjusted throughout in order to maintain a stable body weight throughout the study. Mice were pair-fed in order to maintain similar caloric intakes in both groups. At the end of the seven weeks, mice were challenged by a 5% weight-load swimming test to exhaustion.

As shown in FIG. 1, it was observed that mice in Group 2 swam for an average of 22% longer than the mice in the non-treated group (p=0.024). This demonstrated that the nutritional blend increased endurance capacity in middle-aged female mice.

Example 8

Effects of Pomegranate-Cordyceps-Ginseng Formulation on Physiological Responses to Exercise in Middle-Aged Male Mice Thirty-two (32) male mice, 18 months old, were randomly assigned to one of two groups. Group 1 (n=16) was fed a regular chow diet, while Group 2 (n=16) was fed a regular chow diet plus a blend of pomegranate extract, *panax ginseng* and *c. sinensis* (800 mg/kg diet, delivered by gavage). Feeding continued for two weeks. Caloric intake was adjusted throughout in order to maintain a stable body weight throughout the study. Mice were pair-fed in order to maintain similar caloric intakes in both groups. At the end of the two weeks, the mice were challenged by a treadmill test to exhaustion. Mice were sacrificed immediately following the treadmill test; tissues were collected and stored frozen for biochemical analyses.

Figure 2:
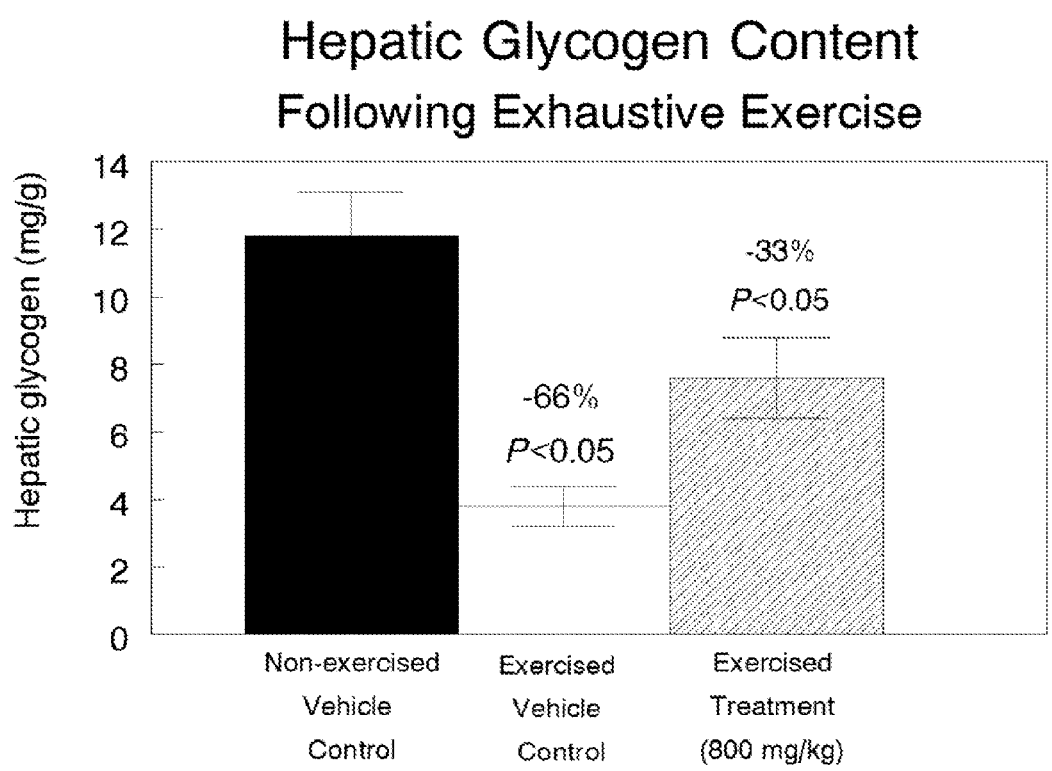
FIG. 2 is a bar graph comparing hepatic glycogen content in mice receiving a formulation in accordance with an embodiment to mice receiving vehicle only.
Figure 3:
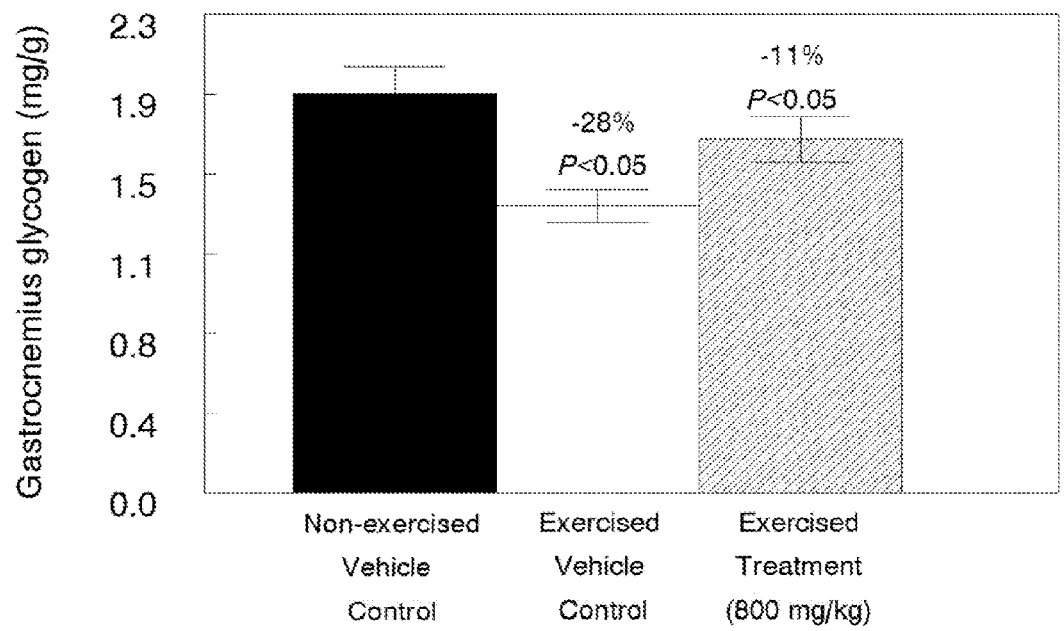
FIG. 3 is a bar graph comparing skeletal muscle glycogen content in the groups of mice represented in FIG. 2.
Figure 4:
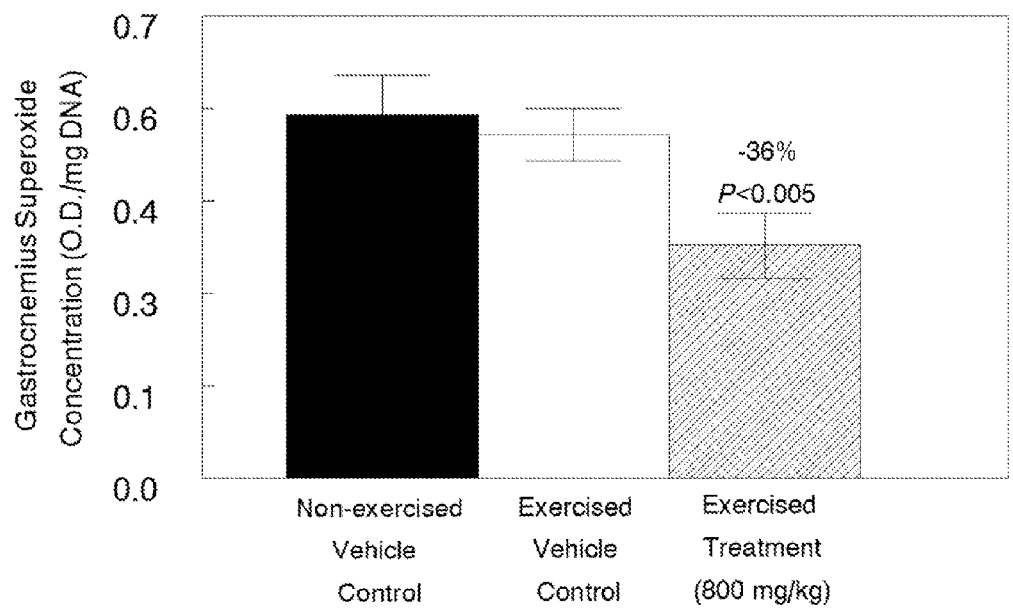
FIG. 4 is a bar graph comparing skeletal muscle superoxide content in the groups of mice represented in FIG. 2.
Figure 5:
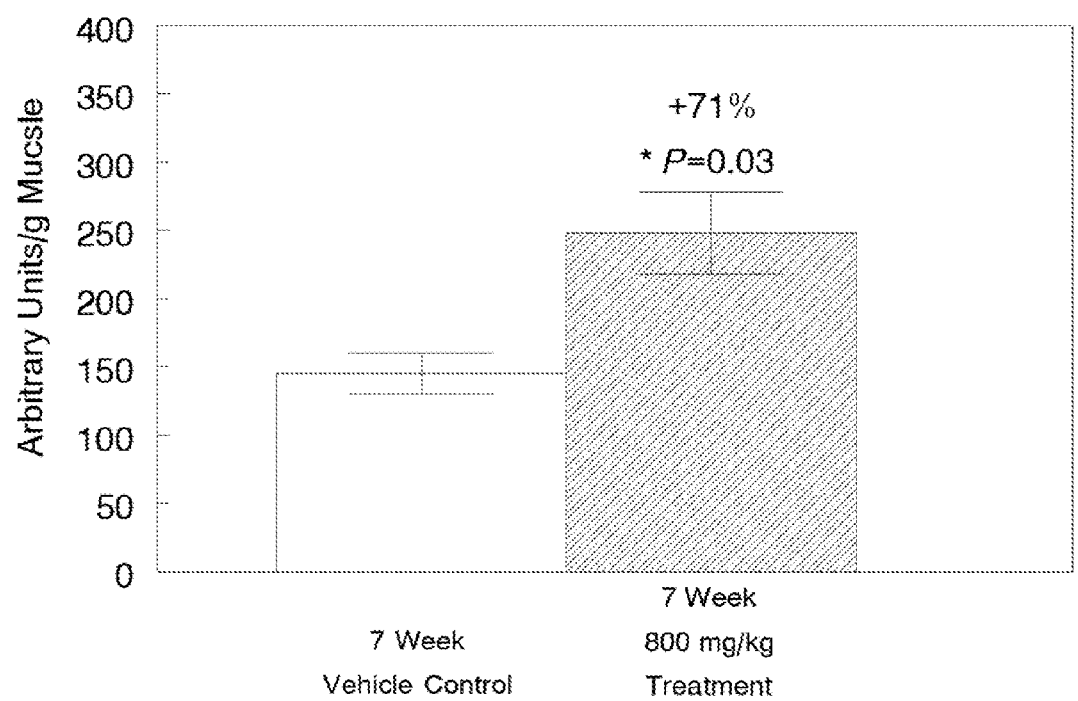
FIG. 5 is a bar graph comparing mitochondrial oxidative phosphorylation protein levels in skeletal muscle in the groups of mice represented in FIG. 2.

At the end of the exercise to exhaustion, mice in the treatment group had greater stores of both liver ($p<0.05$) and skeletal muscle glycogen ($p<0.05$) than the non-treatment group. As shown in FIGS. 2 and 3, following the exhaustive exercise the treated mice had depleted 33% of their liver glycogen and 6% of their muscle glycogen. In contrast, the untreated group had depleted 66% of their liver glycogen and 28% of their muscle glycogen. These results indicate that the treatment effectively spared liver and muscle glycogen during exhaustive endurance exercise. In addition, FIG. 4 shows that the treated mice demonstrated greater resistance to exercise-induced oxidative stress, with 36% lower levels of superoxide in muscles following exercise compared to the non-treatment group (p<0.005). Finally, as shown in FIG. 5, the treated group exhibited 71% higher concentrations of mitochondrial oxidative phosphorylation (OXPHOS) protein levels in skeletal muscle than the control group (p=0.03).

The results indicate that the nutritional blend increased metabolic efficiency and resistance to oxidative stress in middle-aged male mice subjected treadmill test to exhaustion. Increased metabolic efficiency was evidenced by increased fatty acid utilization in lieu of glucose during endurance exercise associated with enhancements in oxidative phosphorylation and glycogen sparing.

Example 9

Effects of Administering Pomegranate-Cordyceps-Ginseng Formulation on Antioxidant Activity in Human Subjects Forty-seven subjects (21 male, 26 female) were recruited to participate in the study. The age range of the subjects was 40-68 years. Subjects were randomized into two test groups: An Experimental group (n=24) which received a pomegranate-Cordyceps-ginseng formulation and a Placebo group (n=23). The form and daily dosages of the experimental formulation and placebo were the same as in Example 9 above. Supplementation continued for eight weeks.

Skin carotenoid levels were measured in each subject using a Pharmanex® Biophotonic Scanner (Nu Skin Co, Provo, Utah) to examine the effects of treatment on antioxidant activity. A measurement taken before treatment commenced (Day 0) provided a baseline, and a subsequent measurement was taken at 4 weeks (Day 28). Raman Intensity Scores were summarized and compared across groups on Day 28 and for change from Day 0 to Day 28.

Table 8 summarizes the Raman Intensity Scores by study day and group. The change in score was significantly higher in the Experimental group than in the Placebo group, with the Experimental group showing a mean increase in score of 595, and the Placebo group a mean decrease of 1777.

Example 10

Evaluation of Formulation Ingredients on Gene Expression in Human Skeletal Muscle Cells In Vitro Clonetics® primary skeletal muscle cells (cat.# CC-2561) were plated with media (cat.# CC-3160) and reagent pack (Trypsin, trypsin neutralizing solution and HEPES buffered saline, cat.# CC-5034, all from Lonza AG, Cologne), into 384-well plates, incubated overnight at 37° C., then treated with either Pomegranate Extract (aqueous solution 5 mcg/mL), *Cordyceps sinensis* (aqueous solution 5 mcg/mL), *panax ginseng* extract (aqueous solution 5 mcg/mL), or a blend of 88.1% *Cordyceps sinensis*, 4.4% *panax ginseng* extract, and 7.5% pomegranate extract in aqueous solution (concentration=5 mcg/mL). Cells were then incubated for 24 hours.

RNA was isolated from skeletal muscle cells and gene expression profiling was performed using Affymetrix® Microarrays to measure global changes in gene expression. RNA was isolated and assessed for concentration and purity using a spectrophotometer. RNA samples were labeled for microarray analysis using the Affymetrix 3' IVT labeling kit and protocol. Human HG U133 Plus 2.0 microarrays that contain 45,000 transcripts were used for the study. All processes were carried out in accordance with Affymetrix recommended protocols.

Data were analyzed using GeneSpring microarray software. T-tests were performed to obtain datasets containing genes that are regulated at a statistically significant level. There were 241 genes that exhibited a significant fold change (i.e. greater than twofold). Of those 241 genes, 187 showed no significant change with treatment by one or more of the individual ingredients. These results indicate an interactive effect arising from the combination of all three ingredients.

What is claimed is:

1. An oral formulation, comprising pomegranate extract, *Panax ginseng* extract, and *Cordyceps sinensis* (*C. sinensis*), each present in an amount effective to counteract effects of aging in a subject when administered to the subject, wherein the oral formulation is more effective to counteract the effects in the subject to a greater degree than any one of pomegranate extract, *Panax ginseng* extract, and *C. sinensis*.

2. The oral formulation of claim 1, further comprising at least one strain selected from *Paecilomyces hepialis* (*P. hepialis*) and *Hirsutella sinensis* (*H. sinensis*).

3. The oral formulation of claim 1, wherein the *Panax ginseng* extract includes ginsenoside Rb1 and ginsenoside Rg1 at a ratio of about 3:1 to about 5:1.

4. The oral formulation of claim 1, wherein the pomegranate extract includes at least 80 wt % polyphenols.

TABLE 8

Results of biophotonic scanner measurements in human subjects

| Raman intensity score | Product | | | | | | |
|---|---|---|---|---|---|---|---|
| | Experimental, n = 24 | | | Placebo, n = 23 | | | p-values, |
| | Day 0 | Day 28 | Change | Day 0 | Day 28 | Change | mean X vs. Y |
| Mean | 21613 | 22208 | +595 | 21684 | 19907 | −1777 | D28, X vs Y |
| SD | 7598 | 7421 | 2983 | 10481 | 9185 | 995 | P = 0.3488† |
| Minimum | 4995 | 7230 | −4447 | 2643 | 2629 | −14016 | Δ, X vs Y |
| Maximum | 38024 | 40477 | +6134 | 40068 | 35454 | 7007 | P = 0.0460† |

†Unpaired t-test

5. The oral formulation of claim 1, further comprising at least one additive selected from the group consisting of a gum, an anti-caking agent, lecithin, microcrystalline cellulose, silica gel, and flavoring.

6. The oral formulation of claim 1, further comprising at least one additional active agent selected from the group consisting of: Schizandra berry extract, whole grape extract, CoenzymeQ$_{10}$, Rhodiola rosacea extract, Tart cherry extract, and L-carnitine tartrate.

7. The oral formulation of claim 1, present in a dosage form selected from the group consisting of: capsule, tablet, powder, beverage, wafer, confectionary, chewable, gel, paste, elixir, syrup, drops, and lozenge.

8. The oral formulation of claim 1, in a dosage form containing about 140 mg to about 200 mg pomegranate extract, from about 70 mg to about 130 mg *Panax ginseng* extract, and from about 1800 mg to about 2200 mg *C. sinensis*.

9. The oral formulation of claim 1, wherein the effect is a decline in energy metabolism.

10. The oral formulation of claim 1, wherein the effect is a decline in sexual performance.

11. The oral formulation of claim 1, wherein the effect includes age-related changes in gene expression.

12. The oral formulation of claim 11, wherein the gene expression is for a biomarker of aging.

13. The oral formulation of claim 11, wherein the gene expression occurs in muscle tissue.

14. The oral formulation of claim 11, wherein the gene expression occurs in brain tissue.

15. The oral formulation of claim 1, wherein the formulation counteracts the effect in the subject to an equivalent or greater degree than caloric restriction in the same subject.

16. An oral formulation comprising: pomegranate extract at about 0.09 wt % to about 80.32 wt %; *Cordyceps sinensis* (*C. sinensis*) at about 13.46 wt % to about 99.67 wt %; and *Panax ginseng* extract at about 0.19 wt % to about 67.72 wt %.

17. The oral formulation of claim 16, wherein pomegranate extract is present at from about 6.5 wt % to about 8.0 wt %, *Panax ginseng* extract is present at from about 3.5 wt % to about 5.0 wt %, and *C. sinensis* is present at from about 83.0 wt % to about 89 wt %.

18. The oral formulation of claim 16, wherein the oral formulation counteracts an effect of aging in a subject when administered to the subject.

19. The oral formulation of claim 18, wherein the effect is a decline in energy metabolism.

20. The oral formulation of claim 18, wherein the effect is a decline in sexual performance.

21. The oral formulation of claim 18, wherein the effect includes age-related changes in gene expression.

22. The oral formulation of claim 21, wherein the gene expression is for a biomarker of aging.

23. The oral formulation of claim 21, wherein the gene expression occurs in muscle tissue.

24. The oral formulation of claim 21, wherein the gene expression occurs in brain tissue.

25. The oral formulation of claim 18, wherein the formulation counteracts the effect in the subject to a similar or greater degree than caloric restriction in the same subject.

26. The oral formulation of claim 18, wherein an amount of the oral formulation counteracts the effect in the subject to a greater degree than an equal amount of any one of pomegranate extract, *Panax ginseng* extract, and *C. sinensis*.

27. The oral formulation of claim 16, further comprising at least one strain selected from *Paecilomyces hepialis* (*P. hepialis*) and *Hirsutella sinensis* (*H. sinensis*).

28. The oral formulation of claim 16, wherein the *Panax ginseng* extract includes ginsenoside Rb1 and ginsenoside Rg1 at a ratio of about 3:1 to about 5:1.

29. The oral formulation of claim 16, wherein the pomegranate extract includes at least 80 wt % polyphenols.

30. The oral formulation of claim 16, further comprising at least one additive selected from the group consisting of a gum, an anti-caking agent, lecithin, microcrystalline cellulose, silica gel, and flavoring.

31. The oral formulation of claim 16, further comprising at least one additional active agent selected from the group consisting of: Schizandra berry extract, whole grape extract, CoenzymeQ$_{10}$, Rhodiola rosacea extract, Tart cherry extract, and L-carnitine tartrate.

32. The oral formulation of claim 16, present in a dosage form selected from the group consisting of: capsule, tablet, powder, beverage, wafer, confectionary, chewable, gel, paste, elixir, syrup, drops, and lozenge.

33. A method of counteracting an effect of aging in a subject, comprising administering to the subject a therapeutically effective amount of the composition of claim 1.

34. The method of claim 33, wherein the therapeutically effective amount delivers to the subject a daily dose comprising about 0.15 mg/kg to about 30.0 mg/kg of pomegranate extract, about 0.35 mg/kg to about 15 mg/kg of *Panax ginseng* extract, and about 15.0 mg/kg to about 150.0 mg/kg of *C. sinensis*.

35. The method of claim 33, wherein the oral formulation includes pomegranate extract at about 0.09 wt % to about 80.32 wt %; *C. sinensis* at about 13.46 wt % to about 99.67 wt %; and *Panax ginseng* extract at about 0.19 wt % to about 67.72 wt %.

36. The method of claim 33, wherein the subject is human.

37. The method of claim 33, wherein the composition further comprises at least one strain selected from *Paecilomyces hepialis* (*P. hepialis*) and *Hirsutella sinensis* (*H. sinensis*).

38. The method of claim 33, wherein the *Panax ginseng* extract includes ginsenoside Rb1 and ginsenoside Rg1 at a ratio of about 3:1 to about 5:1.

39. The method of claim 33, wherein the pomegranate extract includes at least 80 wt % polyphenols.

40. The method of claim 33, further comprising at least one additive selected from the group consisting of a gum, an anti-caking agent, lecithin, microcrystalline cellulose, silica gel, and flavoring.

41. The method of claim 33, further comprising at least one additional active agent selected from the group consisting of: Schizandra berry extract, whole grape extract, CoenzymeQ10, Rhodiola rosacea extract, Tart cherry extract, and L-carnitine tartrate.

42. The method of claim 33, wherein the oral formulation is present in a dosage form selected from the group consisting of: capsule, tablet, powder, beverage, wafer, confectionary, chewable, gel, paste, elixir, syrup, drops, and lozenge.

43. The method of claim 33, wherein the effect is a decline in energy metabolism.

44. The method of claim 33, wherein the effect is a decline in sexual performance.

45. The method of claim 33, wherein the effect includes age-related changes in gene expression.

46. The method of claim 45, wherein the gene expression is for a biomarker of aging.

47. The method of claim 45, wherein the gene expression occurs in muscle tissue.

48. The method of claim 45, wherein the gene expression occurs in brain tissue.

49. The method of claim 45, wherein the formulation counteracts the effect in the subject to a similar or greater degree than caloric restriction in the same subject.

50. A method of counteracting changes in gene expression in a tissue, comprising treating the tissue with a therapeutically effective amount of the composition of claim 1.

51. The method of claim 50, wherein the changes in gene expression are a function of the age of a subject from which the tissue is obtained.

52. The method of claim 50, wherein the composition further comprises at least one strain selected from *Paecilomyces hepialis* (*P. hepialis*) and *Hirsutella sinensis* (*H. sinensis*).

53. The method of claim 50, wherein the pomegranate extract includes at least 80 wt % polyphenols.

54. The method of claim 50, wherein the *Panax ginseng* extract includes ginsenoside Rb1 and ginsenoside Rg1 at a ratio of about 3:1 to about 5:1.

55. The method of claim 50, wherein the oral formulation includes pomegranate extract at about 0.09 wt % to about 80.32 wt %; *C. sinensis* at about 13.46 wt % to about 99.67 wt %; and *Panax ginseng* extract at about 0.19 wt % to about 67.72 wt %.

* * * * *